(12) United States Patent
Kakuta (10) Patent No.: US 10,850,040 B2
(45) Date of Patent: Dec. 1, 2020

(54) SYRINGE-TYPE EJECTOR

(71) Applicant: Yoshiyuki Kakuta, Tokyo (JP)

(72) Inventor: Yoshiyuki Kakuta, Tokyo (JP)

(73) Assignee: YOSHINO KOGYOSHO CO., LTD., Tokyo (JP)

( * ) Notice: Subject to any disclaimer, the term of this patent is extended or adjusted under 35 U.S.C. 154(b) by 266 days.

(21) Appl. No.: 15/767,865

(22) PCT Filed: Aug. 18, 2016

(86) PCT No.: PCT/JP2016/003784
§ 371 (c)(1),
(2) Date: Apr. 12, 2018

(87) PCT Pub. No.: WO2017/072992
PCT Pub. Date: Apr. 5, 2017

(65) Prior Publication Data
US 2018/0296766 A1    Oct. 18, 2018

(30) Foreign Application Priority Data

Oct. 29, 2015   (JP) .............................. JP2015-213403

(51) Int. Cl.
*A61M 5/315*   (2006.01)
*A61M 5/50*    (2006.01)

(52) U.S. Cl.
CPC ........ *A61M 5/31566* (2013.01); *A61M 5/315* (2013.01); *A61M 5/3159* (2013.01);
(Continued)

(58) Field of Classification Search
CPC .............. A61M 5/31566; A61M 5/315; A61M 5/31511; A61M 5/3159; A61M 5/31595
See application file for complete search history.

(56) References Cited

U.S. PATENT DOCUMENTS

2013/0085457 A1*   4/2013   Schiff ................ A61M 5/31511
                                                             604/228

FOREIGN PATENT DOCUMENTS

EP    2 832 452 A1    2/2015
JP    H07-213612 A    8/1995
(Continued)

OTHER PUBLICATIONS

May 6, 2019 Extended Search Report issued in European Patent Application No. 16859233.5.
(Continued)

*Primary Examiner* — Nathan R Price
*Assistant Examiner* — Melissa A Snyder
(74) *Attorney, Agent, or Firm* — Oliff PLC (57) ABSTRACT

The syringe dispenser includes a syringe and a plunger. The plunger includes a first shaft member including a piston and second shaft member configured to be fitted in a tubular portion of the first shaft member. The first shaft member includes an elastic piece, the elastic piece being provided with a slide projection configured to slide on an inner surface of the syringe and a lock projection configured to be locked against the syringe. The second shaft member includes a pressing shaft configured to be fitted in the tubular portion. The pressing shaft is provided in a front end thereof with an end surface configured to press a free end of the elastic piece. In response to pressing from the end surface, the lock projection is locked against the rear end of the syringe, and in response to the pressing being released, the locking of the lock projection is released.

7 Claims, 11 Drawing Sheets

(52) U.S. Cl.
CPC .... *A61M 5/31511* (2013.01); *A61M 5/31595* (2013.01); *A61M 5/5013* (2013.01)

(56) References Cited

FOREIGN PATENT DOCUMENTS

| | | |
|---|---|---|
| JP | 2012-249716 A | 12/2012 |
| JP | 2013-208603 A | 10/2013 |
| JP | 2013-248107 A | 12/2013 |
| JP | 2015-104574 A | 6/2015 |

OTHER PUBLICATIONS

May 1, 2018 International Preliminary Report on Patentability issued in International Patent Application No. PCT/JP2016/003784.
Nov. 15, 2016 International Search Report issued in International Patent Application No. PCT/JP2016/003784.
Feb. 6, 2020 Office Action issued in Chinese Patent Application No. 201680061885.3.
Sep. 23, 2020 Office Action issued in Chinese Patent Application No. 201680061885.3.

* cited by examiner

A-A section

SYRINGE-TYPE EJECTOR

CROSS-REFERENCE TO RELATED APPLICATION

The present application claims priority to and the benefit of Japanese Patent Application No. 2015-213403 filed on Oct. 29, 2015, the entire contents of which are incorporated herein by reference.

TECHNICAL FIELD

The present disclosure relates to a syringe-type ejector (hereinafter, called a syringe dispenser) including a syringe and a plunger configured to be pushed into the syringe, and the present disclosure also relates to a technology for pushing the plunger in a stepwise fashion.

BACKGROUND

Examples of syringe dispensers include those that are configured to dispense a content medium such as a medicinal fluid in response to a plunger being pushed into a syringe (refer, for example, to Patent Literature 1).

However, it has been difficult for such a conventional syringe dispenser in which the plunger is merely pushed into the syringe to divide the amount of the content medium into smaller fractions to be dispensed.

To address the above problem, Patent Literature 2 describes a syringe dispenser that is capable of dispensing the content medium in two parts by pushing the plunger in two steps.

CITATION LIST

Patent Literatures

PTL1: JPH07213612A
PTL2: JP2013208603A

SUMMARY

Technical Problem

In the syringe dispenser described in Patent Literature 2, the plunger is configured by two shafts, and there is room for improvement in terms of operability based on cooperation of the shafts.

The present disclosure is to provide a syringe dispenser that is configured to divide the amount of the content medium into smaller fractions to be dispensed and that also provides improved operability.

Solution to Problem

To solve the above problem, one of aspects of the present disclosure resides in a syringe dispenser including: a syringe; and a plunger configured to be pushed into the syringe. The plunger includes: a first shaft member including a piston at a front end thereof; and a second shaft member configured to be fitted in a tubular portion of the first shaft member. The first shaft member includes at least one elastic piece extending toward a rear side, the elastic piece being provided with a slide projection and a lock projection, the slide projection being configured to enter through a rear end opening portion of the syringe and slide on an inner circumferential surface of the syringe, and the lock projection being configured to be locked against a rear end of the syringe. The second shaft member includes a pressing shaft configured to be fitted in the tubular portion, the pressing shaft being provided in a front end thereof with an end surface configured to press a free end of the elastic piece, and the pressing shaft being also provided on an outer circumferential surface thereof with an engagement projection configured to engage with an engagement portion of the tubular portion to prevent the second shaft member from slipping out of the tubular portion. In response to pressing from the end surface, the free end of the elastic piece is restrained between the second shaft member and the syringe, and the elastic piece undergoes a flexure deformation starting from the slide projection, and thus, the lock projection is locked against the rear end of the syringe, and in response to the pressing being released, the locking of the lock projection is released due to a restoring force from the flexure deformation that starts from the slide projection.

Preferably, the tubular portion is provided with an opening penetrating in a radial direction, and the elastic piece is arranged within the opening, with a rear end edge of the opening serving as the engagement portion.

Preferably, a position of the end surface when the pressing is released is determined by the engagement projection abutting against the engagement portion of the tubular portion.

Preferably, the slide projection and the lock projection are coupled by a thinned portion having a thickness in a radial direction that is reduced.

Preferably, the elastic piece, in a portion from a base portion to the slide projection thereof, is formed to have a thickness in a radial direction that is gradually increased.

Preferably, the end surface is provided with a tapered surface.

Preferably, the first shaft member is provided on an outer circumferential surface thereof with a rib configured to engage with the rear end of the syringe in a position in which the pressing is started.

Advantageous Effect

The present disclosure provides a syringe dispenser that is configured to divide the amount of the content medium into smaller fractions to be dispensed and that also provides improved operability.

DETAILED DESCRIPTION

The following describes a syringe dispenser 1 according to one of embodiments of the present disclosure in detail with reference to the drawings.

Figure 1A:
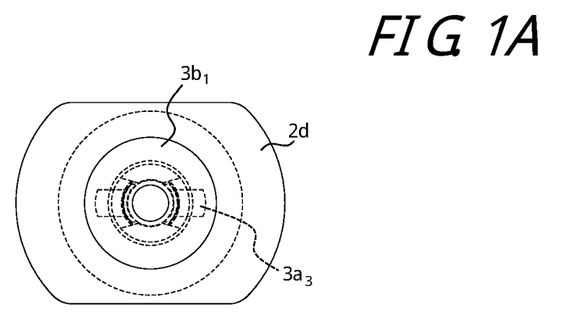
FIG. 1A is a plan view of a syringe dispenser in an initial state before operation according to one of embodiments of the present disclosure.
Figure 1B:
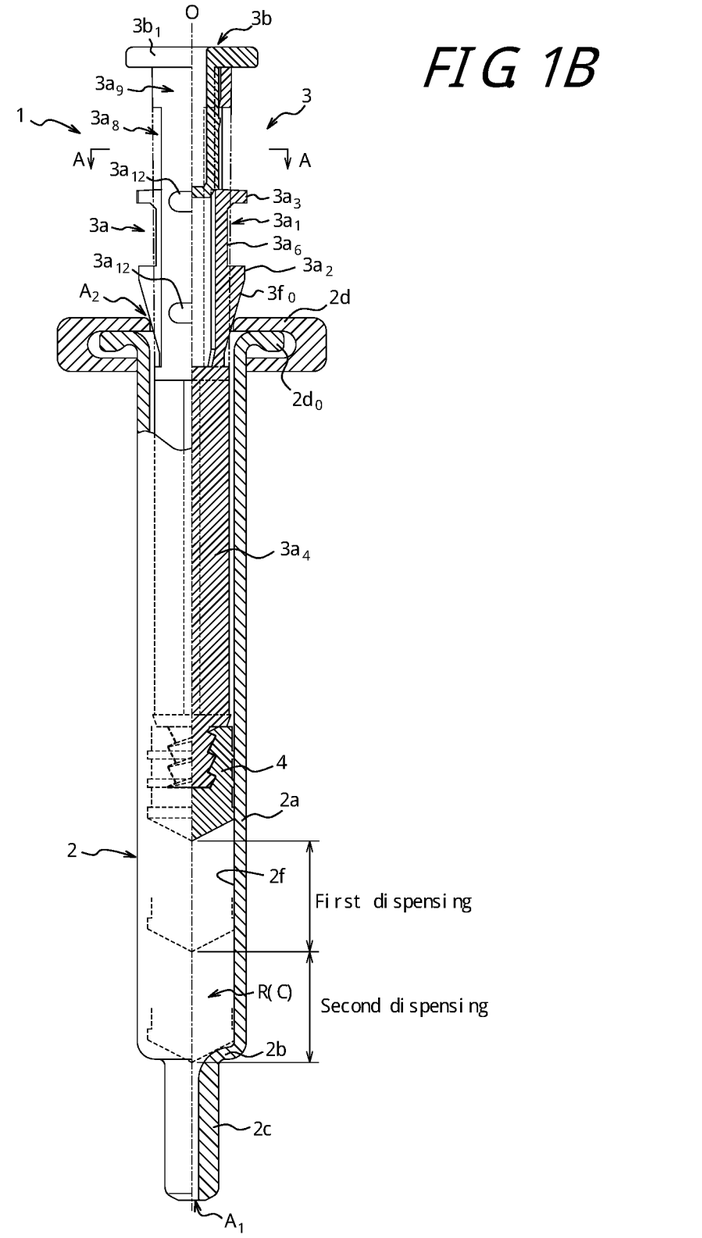
FIG. 1B is a front partial sectional view of the syringe dispenser in the initial state before operation according to the one of embodiments.
Figure 1C:
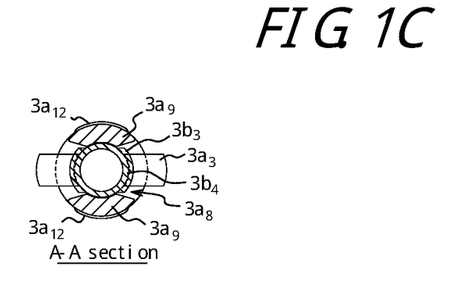
FIG. 1C is a sectional view along an A-A section of a plunger that is used in the syringe dispenser in the initial state before operation according to the one of embodiments.

In FIG. 1B, reference numeral 2 denotes a syringe in which a content medium C, such as a medicine, may be filled. Note that in the specification, claims, abstract, and drawings, the direction (i.e., downward direction in FIG. 1B) in which the content medium C is dispensed is defined as a front side, and the side (i.e., upward direction in FIG. 1B) in which a second shaft portion $3b$ is located is defined as a rear side. The syringe 2 includes a hollow trunk $2a$ and a front end portion $2c$, which is integrally connected to the trunk $2a$ via a shoulder $2b$. The front end portion $2c$ has a diameter that is smaller than that of the trunk $2a$. The syringe 2 also includes, at a rear end of the trunk $2a$, a syringe's rear end portion $2d_0$, whose diameter is increased, and a flange portion $2d$, which is fitted to the syringe's rear end portion $2d_0$. That is to say, the flange portion $2d$ constitutes the rear end of the syringe 2.

Reference numeral 3 refers to a plunger configured to be accommodated in the syringe 2. The plunger 3 includes a first shaft member $3a$ and the second shaft member $3b$, which is arranged at the rear of the first shaft member $3a$.

The first shaft member $3a$ includes a piston 4 at a front end portion of the first shaft member $3a$ that is configured to be accommodated in the syringe 2. The piston 4 is made of an elastic material, such as rubber, and is slidably held on an inner circumferential surface $2f$ of the syringe trunk $2a$.

Between the syringe 2 and the piston 4, space R is defined. The space R is configured to be filled with the content medium C. The content medium C filled in the space R is pressure-fed to a front end through hole $A_1$, which is provided in the front end portion $2c$, in response to the plunger 3 being pushed in.

Figure 5:
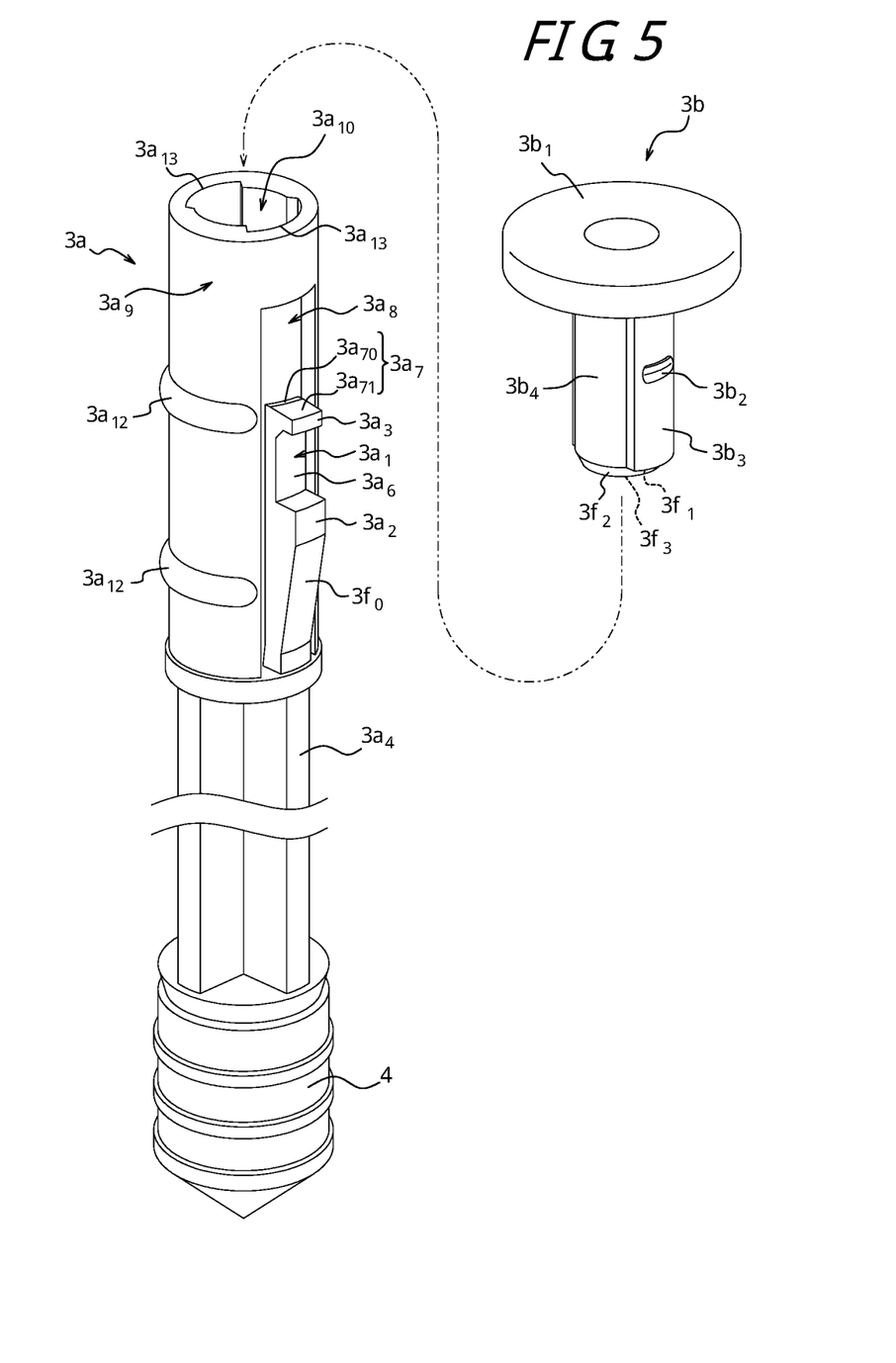
FIG. 5 is a perspective view of the first shaft member and the second shaft member that constitute the plunger used in the syringe dispenser according to the one of embodiments.

As illustrated in FIG. 5, the first shaft member $3a$ includes a tubular portion $3a_9$, which is disposed on the rear side of the first shaft member $3a$. The tubular portion $3a_9$ has a circumferential wall provided with an opening $3a_8$, which penetrates in the radial direction. The opening $3a_8$ communicates with a tubular portion's insertion hole $3a_{10}$, into which the second shaft $3b$ is to be inserted.

As illustrated in FIG. 1B, the first shaft member $3a$ is provided integrally with two elastic pieces $3a_1$, which extend toward the rear side. Each elastic piece $3a_1$ is provided with a slide projection $3a_2$ and a lock projection $3a_3$. The slide projection $3a_2$ and the lock projection $3a_3$ are disposed at an interval along an axis line O toward the rear side in the order of the slide projection $3a_2$ and the lock projection $3a_3$. The slide projection $3a_2$ has a tapered portion $3f_0$, which tapers toward a front end thereof. With the above configuration, the slide projection $3a_2$ may enter through a rear end opening portion $A_2$ of the syringe 2 and slide on the inner circumferential surface $2f$ of the syringe 2, and accordingly, permit the plunger 3 to be pushed in. Furthermore, the slide projection $3a_2$ and the lock projection $3a_3$ are coupled by a thinned portion $3a_6$ so that the elastic piece $3a_1$ may easily undergo a flexure deformation starting from the slide projection $3a_2$. As described later, the lock projection $3a_3$ is configured to be caught against an inner circumferential end of the flange portion $2d$, which is disposed at the rear end of the syringe 2, to prevent the plunger 3 from being pushed in further. As illustrated in FIG. 5, the elastic piece $3a_1$ is arranged to be accommodated within the opening $3a_8$. As illustrated in FIG. 1B, an outer diameter of the slide projection $3a_2$ in an initial state (initial position) is larger than an inner diameter of the syringe 2.

As illustrated for example in FIGS. 1B and 5, the first shaft member $3a$ includes a base portion $3a_4$, to which the piston 4 is fixed, and the elastic pieces $3a_1$ are coupled to a rear end of the base portion $3a_4$. The base portion $3a_4$ may adopt, for example, a shape as illustrated in FIG. 5 in which two wall surfaces extending in the front-rear direction (i.e., vertical direction in FIG. 5) to form a cross-shaped sectional shape are arranged between a disc-shaped front wall and a disc-shaped rear wall in a manner such that the two wall surfaces cross each other at right angles. The above configuration allows each elastic piece $3a_1$, on the free end side thereof that is provided with the lock projection $3a_3$, to undergo flexure deformation in a manner such that the elastic piece $3a_1$ may be deformed and restored, with a portion of the elastic piece $3a_1$ coupled to the base portion $3a_4$ serving as a fixed end. The hollow cylindrical-shaped tubular portion $3a_9$ is also coupled to the rear end of the base portion $3a_4$.

Figure 3A:
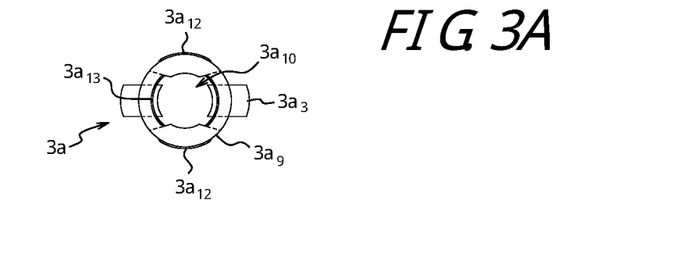
FIG. 3A a plan view of a first shaft member that is used in the syringe dispenser according to the one of embodiments.
Figure 3B:
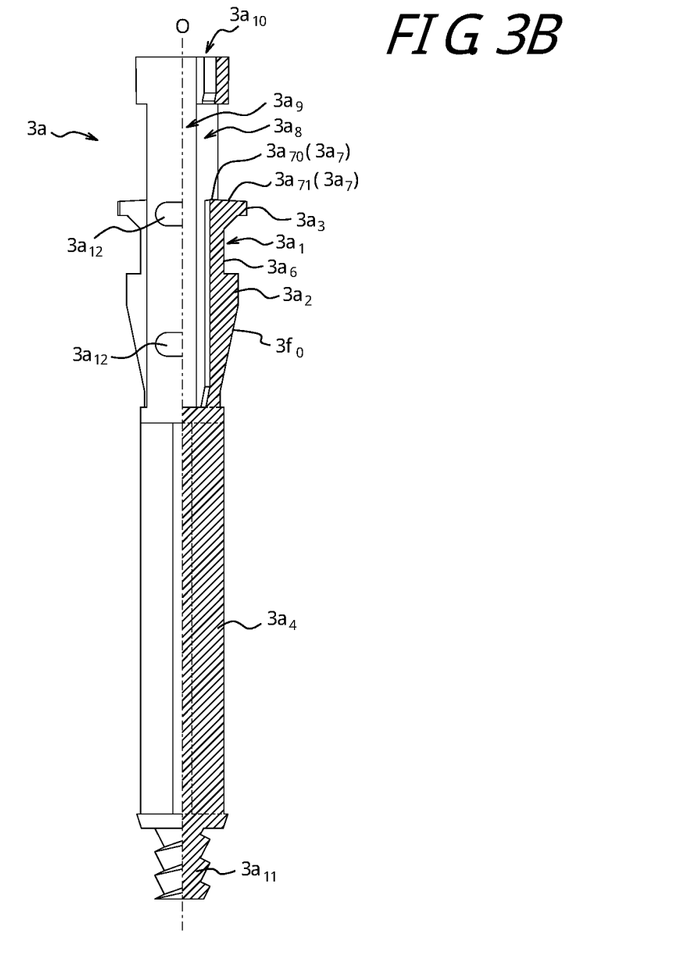
FIG. 3B is a front half-sectional view of the first shaft member that is used in the syringe dispenser according to the one of embodiments.

The lock projection $3a_3$ is formed on the free end side of the elastic piece $3a_1$ in an integrated manner. As illustrated in FIGS. 3B and 5, a rear end surface of the lock projection $3a_3$ is formed as a pressed surface $3a_7$, which is configured to receive pressing force from the second shaft member $3b$. As illustrated in FIG. 3B, the pressed surface $3a_7$ is configured by a pressed flat surface $3a_{70}$, which extends in the horizontal direction at an inner end of the pressed surface $3a_7$ in the radial direction, and a pressed tapered surface $3a_{71}$, which is disposed on the outer circumferential side of the pressed flat surface $3a_{70}$. The pressed tapered surface $3a_{71}$ has a tapered surface that slightly tapers toward the front side in the outer circumferential direction. As described later, the pressed flat surface $3a_{70}$ serves as a surface configured to receive pressing force from the second shaft member $3b$ in a first dispensing of the content medium C. The pressed tapered surface $3a_{71}$ serves as a surface configured to receive pressing force from the second shaft member $3b$ in a second dispensing of the content medium C.

Figure 2:
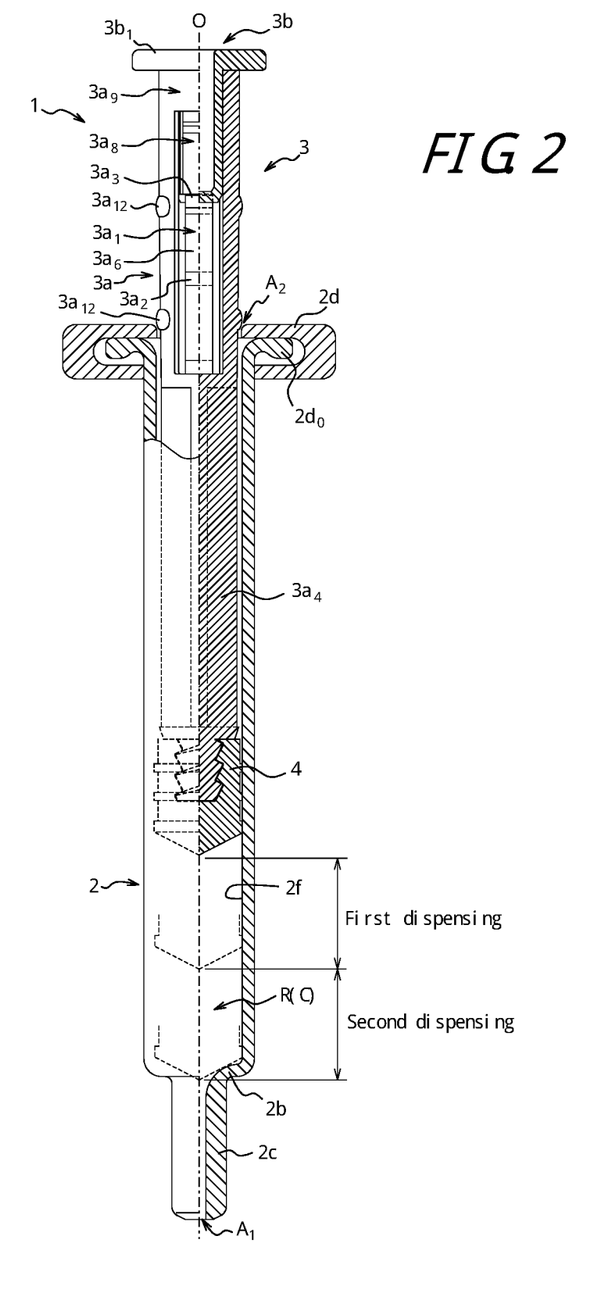
FIG. 2 is a left-side partial sectional view of the syringe dispenser in the initial state before operation according to the one of embodiments.

As illustrated for example in FIGS. 2 and 5, the tubular portion $3a_9$ is provided, on an outer surface thereof, with ribs $3a_{12}$ disposed in two positions along the front-rear direction (i.e., two positions along the vertical direction in FIG. 2). The rib $3a_{12}$ on the front side is disposed so that this rib $3a_{12}$ engages with the inner circumferential end of the flange portion $2d$ in a position of the plunger 3 in which the first dispensing of the content medium C is started. Similarly, the rib $3a_{12}$ on the rear side is disposed so that this rib $3a_{12}$ engages with the inner circumferential end of the flange portion $2d$ of the plunger 3 in which the second dispensing of the content medium C is started. The above configuration allows a user of the syringe dispenser 1 to orient the front end through hole $A_1$ toward an object of dispensing in the positions in which the ribs $3a_{12}$ engage with the inner circumferential end of the flange portion $2d$. The ribs $3a_{12}$ are also configured to climb over the inner circumferential end of the flange portion $2d$ by the user pressing the plunger 3, and this ensures that the content medium C may be dispensed to the object. Additionally, a certain level of pressing force is necessary for the ribs $3a_{12}$ to climb over the inner circumferential end of the flange portion $2d$. Accordingly, the user is to push in the plunger 3 with elevated pressing force, and the content medium C is dispensed with great force. This is especially preferable when the content medium C is dispensed (sprayed) in the form of spray.

Figure 4A:
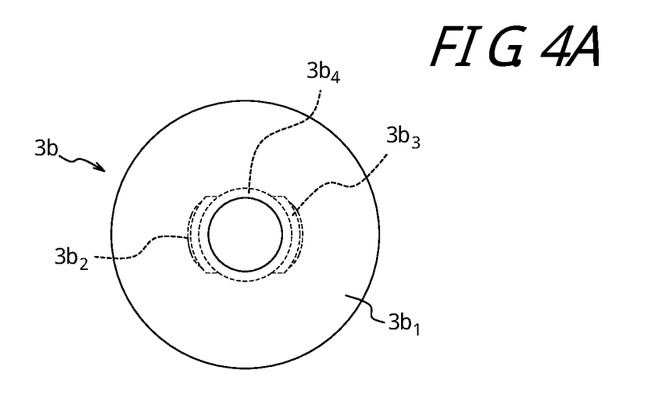
FIG. 4A a plan view of a second shaft member that is used in the syringe dispenser according to the one of embodiments.
Figure 4B:
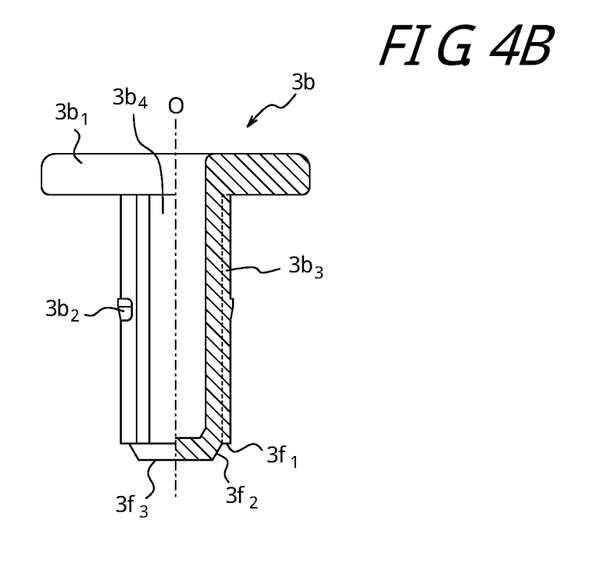
FIG. 4B a front half-sectional view of the second shaft member that is used in the syringe dispenser according to the one of embodiments.

FIGS. 4A and 4B are a plan view and a front half-sectional view of the second shaft member $3b$. As illustrated in FIG. 4B, the second shaft member $3b$ is configured by a pressing shaft $3b_4$ and a pressing flange $3b_1$, which is disposed on the rear side of (i.e., above in FIG. 4B) the pressing shaft $3b_4$ and which is used by the user to push in the plunger 3. As illustrated in FIG. 4B, the pressing shaft $3b_4$ has a bottomed tubular shape with a front end surface $3f_3$ formed as a flat surface that is orthogonal to the axis line O. Additionally, the pressing shaft $3b_4$ may have other shapes, such as a hollow tubular shape, a topped tubular shape, and a solid tubular shape, than the bottomed tubular shape. Furthermore, the pressing flange $3b_1$ may be omitted. As illustrated in FIG. 4A, the pressing shaft $3b_4$ is provided, on an outer surface thereof, with large-diameter portions $3b_3$ disposed in opposing positions on the circumference. At a front end (i.e., lower end in FIG. 4B) of each large-diameter portion $3b_3$, a pressing end surface $3f_1$, which is configured to abut against the pressed surface $3a_7$ of the first shaft member $3a$ to transmit pressing force, is provided. On an outer surface of the large-diameter portion $3b_3$, an engagement projection $3b_2$ is further provided. The engagement projection $3b_2$ is configured to engage with the opening $3a_8$, which is provided in the tubular portion $3a_9$, to prevent the second shaft member $3b$ from slipping out of the tubular portion $3a_9$ when the second shaft member $3b$ is inserted into the tubular portion's insertion hole $3a_{10}$ of the first shaft member $3a$. Additionally, the way to engage the engagement projection $3b_2$ is not limited to the above mode. For example, a projection may be provided on an inner circumferential surface of the tubular portion $3a_9$, and the engagement projection $3b_2$ may be configured to climb over the projection. As illustrated for example in FIG. 5, the tubular portion's insertion hole $3a_{10}$ of the first shaft member $3a$ is provided with large-diameter grooves $3a_{13}$. When the second shaft member $3b$ is inserted into the tubular portion's insertion hole $3a_{10}$, the large-diameter portions $3b_3$ are engaged in the large-diameter grooves $3a_{13}$ of the first shaft member $3a$. The above configuration improves the ease of assembly by allowing alignment in the circumferential direction to be performed at the same time as inserting the second shaft member $3b$ into the first shaft member $3a$. Additionally, the large-diameter portions $3b_3$ and the large-diameter grooves $3a_{13}$ are not indispensable configurations, and the tubular portion's insertion hole $3a_{10}$ and the pressing shaft $3b_4$ may have cylindrical-shaped side surfaces. On the inner circumferential side of the pressing end surface $3f_1$, a tapered surface $3f_2$ is disposed over the entire circumference.

Next, how to use the present embodiment is described with reference to an example where a nasal drop is used as the content medium C.

Figure 6A:
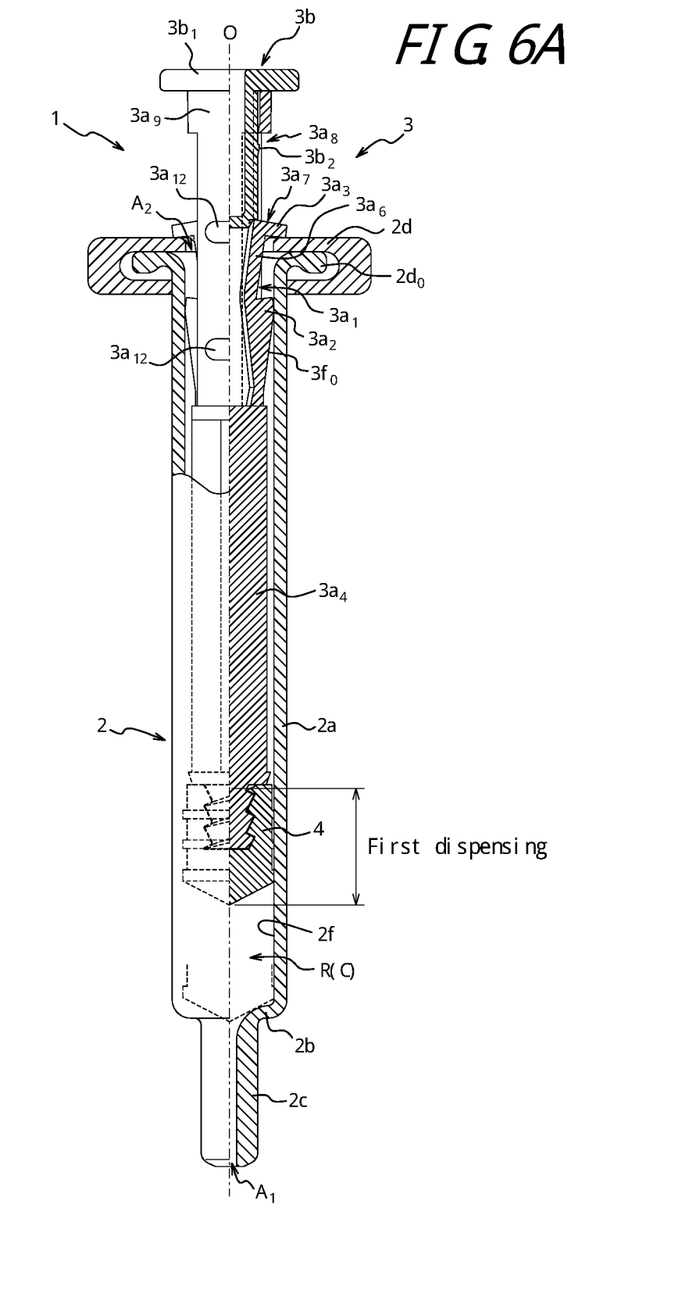
FIG. 6A is a front partial sectional view illustrating a state where a first dispensing by the syringe dispenser according to the one of embodiments is completed.
Figure 6B:
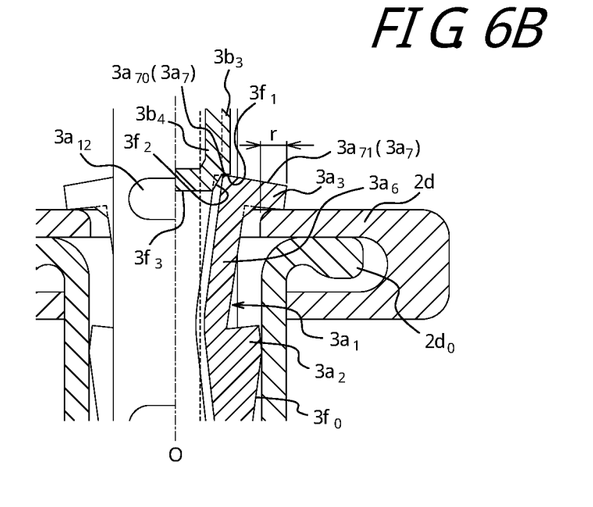
FIG. 6B is an enlarged view of a flange portion illustrated in FIG. 6A.

Firstly, the user inserts the front end portion $2c$ into one of the nostrils in the state where the front rib $3a_{12}$ is in abutment against the inner circumferential end of the flange portion $2d$ as illustrated in FIG. 2. Subsequently, the user pushes in the pressing flange $3b_1$ of the second shaft member $3b$ toward the front side. At this time, since the pressing shaft $3b_4$ of the second shaft member $3b$ is inserted into the tubular portion $3a_9$ of the first shaft member $3a$, reliable pressing operation is achieved without causing the second shaft member $3b$ to stagger or tilt with respect to the first shaft member $3a$ when the second shaft member $3b$ is pressed. Then, as illustrated in FIG. 6B, each pressing end surface $3f_1$, which is provided in the second shaft member $3b$, abuts against the pressed surface $3a_7$, which is disposed on the rear end surface of the corresponding lock projection $3a_3$ of the first shaft member $3a$. At this time, the pressing end surface $3f_1$ abuts against the pressed flat surface $3a_{70}$ of the pressed surface $3a_7$ that is disposed on the inner circumferential side. Consequently, the first shaft member $3a$, together with the second shaft member $3b$, is pushed in toward the front side. At this time, since the slide projection $3a_2$ of the first shaft member $3a$ has the tapered portion $3f_0$, which tapers toward the front end, the first shaft member $3a$ enters the syringe 2 through the syringe's rear end opening portion $A_2$.

Since the pressing end surface $3f_1$ of the second shaft member $3b$ contacts and presses the pressed flat surface $3a_{70}$ of each elastic piece $3a_1$, the movement of the free end of the elastic piece $3a_1$ is restrained between the pressing end surface $3f_1$ and the syringe 2. As a result, as illustrated in FIG. 6A, the elastic piece $3a_1$ undergoes a flexure deformation starting from the slide projection $3a_2$. Herein, the deformation of the pressed surface $3a_7$ toward the inner side in the radial direction is regulated by the pressing end surface $3f_1$ and the tapered surface $3f_2$, and accordingly, the lock projection $3a_3$ remains in the initial position on the free end of the elastic piece $3a_1$. Additionally, the outer diameter or the like of the second shaft member $3b$ may also be altered as appropriate to displace the free end toward the outer circumferential side. By the slide projection $3a_2$ sliding on the inner circumferential surface $2f$ of the syringe 2 while undergoing the aforementioned flexure deformation, the plunger 3 is allowed to be pushed in. The above processes are used to dispense a metered amount of the content medium C (nasal drop) from the front end through hole $A_1$ into the nostril until the lock projection $3a_3$ of the elastic piece $3a_1$ comes into contact with the rear end of the flange portion $2d$ as illustrated in FIG. 6B.

Once the lock projection $3a_3$ of the elastic piece $3a_1$ comes into contact with the rear end of the flange portion $2d$, the plunger 3 cannot be pushed in anymore. Accordingly, the first dispensing is ended while a certain amount of the content medium C (nasal drop) still remains in the space R. Additionally, the volume of the content medium C dispensed for the first time may be determined as appropriate in accordance with intended use. For example, the volume of the content medium C dispensed for the first time may be half the volume of the space R illustrated in FIG. 1B.

Figure 7A:
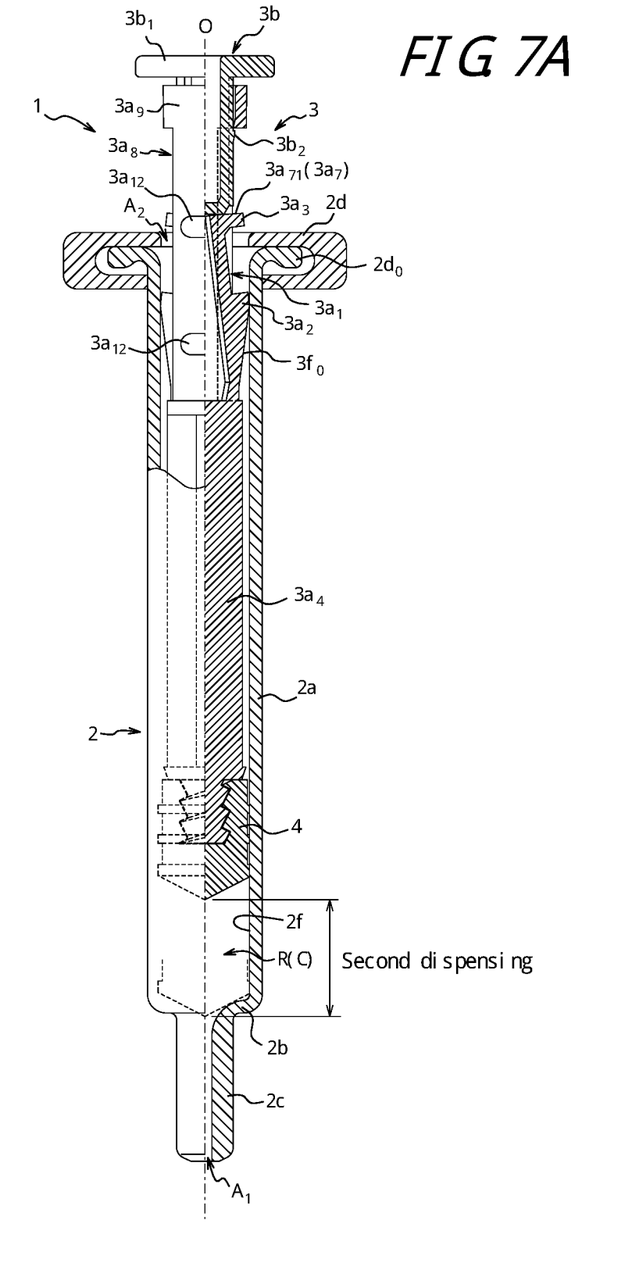
FIG. 7A is a front partial sectional view illustrating a state where preparation for a second dispensing by the syringe dispenser according to the one of embodiments is completed.

Subsequently, when the pressing of the second shaft member $3b$ is released, as illustrated in FIG. 7A, the free end side of the elastic piece $3a_1$ undergoes restoration starting from the slide projection $3a_2$ due to a restoring force from the aforementioned flexure deformation. At this time, the second shaft member $3b$ is pushed back to the rear side by the restoring force of the elastic piece $3a_1$, and, as illustrated in FIG. 7A, the engagement projection $3b_2$, which is provided in the second shaft member $3b$, returns to a rear end of the opening $3a_8$ of the first shaft member $3a$. Furthermore, since the fixed end side of the elastic piece $3a_1$ remains deformed to be displaced toward the inner circumferential side as it extends toward the rear side, the free end side of the elastic piece $3a_1$ is restored toward the inner circumferential direction so that the free end side is aligned with the fixed end side as illustrated in FIG. 7A. Accordingly, the lock projection $3a_3$ also follows the free end side of the elastic piece $3a_1$ and is deformed toward the inner circumferential direction, and as illustrated in FIG. 7A, the locked state of the lock projection $3a_3$ is released. Additionally, since the engagement projection $3b_2$ serves to prevent the second shaft member $3b$ from slipping out, once the engagement projection $3b_2$ comes into abutment against the rear end of the opening $3a_8$, the second shaft member $3b$ will not be displaced to the rear side any further.

Figure 7B:
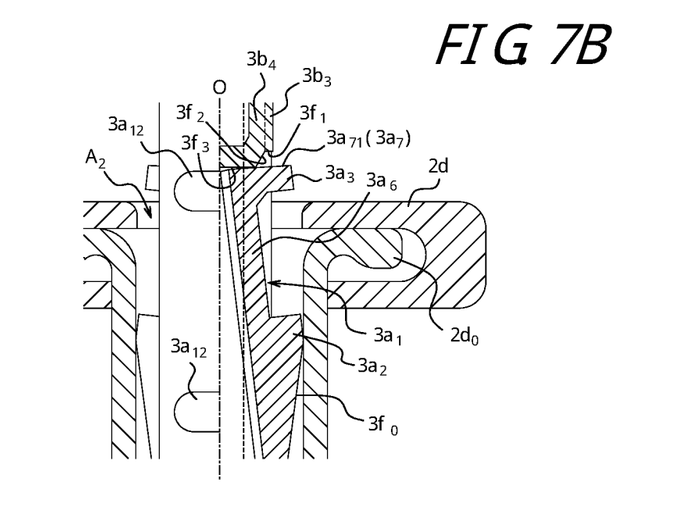
FIG. 7B is an enlarged view of the flange portion illustrated in FIG. 7A.

Especially in the present embodiment, as illustrated in FIG. 7B, since the tapered surface $3f_2$ is disposed on the inner circumferential side of the pressing end surface $3f_1$, the second shaft member $3b$ is pushed back to the rear side due to the aforementioned restoring force when the pressing of the second shaft member $3b$ is released, and the lock projection $3a_3$ previously in abutment against the pressing end surface $3f_1$ may be displaced toward the inner circumferential direction along the tapered surface $3f_2$. Additionally, although in the present embodiment the second shaft member $3b$ is configured to be pushed back to the rear side due to the restoring force of the elastic piece $3a_1$ when the pressing is released, the present disclosure is not limited to this embodiment, and the second shaft member $3b$ may also be configured to be pulled back to the rear side in response to the user pulling the second shaft member $3b$. Furthermore, since the slide projection $3a_2$ and the lock projection $3a_3$ are coupled by the thinned portion $3a_6$, the lock projection $3a_3$ is configured to be displaced toward the inner circumferential side more significantly when the pressing of the second shaft member $3b$ is released. Moreover, as illustrated in the enlarged view of FIG. 7B, the pressed tapered surface $3a_{71}$ is provided on the pressed surface $3a_7$ on the free end of the elastic piece $3a_1$, and the pressed tapered surface $3a_{71}$ slightly tapers toward the front side in the outer circumferential direction. With the above configuration, as illustrated in FIG. 7B, even when the lock projection $3a_3$ of the elastic piece $3a_1$ is displaced toward the inner circumferential direction due to the flexure deformation starting from the slide projection $3a_2$, the deformation of the free end of the elastic piece $3a_1$ in the radial direction is not interfered with by the second shaft member $3b$. Thus, the deformation of the lock projection $3a_3$ toward the inner circumferential direction is not interfered with by the second shaft member $3b$.

In this way, in the present embodiment, the lock projection $3a_3$ is configured to be displaced to a great extent toward the inner circumferential direction when the pressing of the second shaft member $3b$ is released. The above configuration allows a large overlap allowance r between the lock projection $3a_3$ and the rear end of the flange portion $2d$ that helps stop the first dispensing of the content medium C (refer to FIG. 6B). Accordingly, the first dispensing of the content medium C may be stopped reliably.

After the pressing of the second shaft member $3b$ is released, the second dispensing may be achieved by pressing the second shaft member $3b$ again in the state where the rear rib $3a_{12}$ is in abutment against the inner circumferential end of the flange portion $2d$ as illustrated in FIG. 7A. That is to say, in the present embodiment, by pressing the second shaft member $3b$ again after releasing the pressing of the second shaft member $3b$, as illustrated in FIG. 7B, the resulting restoration of the elastic piece $3a_1$ that starts from the slide projection $3a_2$ brings the front end surface $3f_3$ of the second shaft member $3b$ into contact with the pressed tapered surface $3a_{71}$. For the above reason, the first shaft member $3a$ may be pushed in by pressing the second shaft member $3b$ again.

Especially in the present embodiment, the pressed tapered surface $3a_{71}$ is tapered toward the front side as it extends to the outer circumferential direction in the initial state. Accordingly, when the free end side of the elastic piece $3a_1$ undergoes the restoration starting from the slide projection $3a_2$, the front end surface $3f_3$ of the second shaft member $3b$ and the pressed tapered surface $3a_{71}$ contact in substantially a parallel state to each other. The above configuration allows the first shaft member $3a$ to be pushed in smoothly.

As illustrated in FIG. 7A, after releasing the pressing of the second shaft member $3b$ to push back the second shaft member $3b$, the user inserts the front end portion $2c$ into the other nostril. The user may dispense the content medium (nasal drop) remaining in the space R to the nostril through the front end through hole $A_1$ simply by pushing in the second shaft member $3b$ again.

Additionally, it is preferable to adjust the heights of the front and rear ribs $3a_{12}$ so that the pressing force necessary for one rib $3a_{12}$ to pass through the inner circumferential end of the flange portion $2d$ at the first dispensing of the content medium C substantially equals the pressing force necessary for the other rib $3a_{12}$ to pass through the inner circumferential end of the flange portion $2d$ at the second dispensing of the content medium C.

As described above, according to the present embodiment, the amount of the content medium C may be divided into smaller fractions to be dispensed. Furthermore, since in the present embodiment the second dispensing is achieved by pressing the second shaft member $3b$ again after releasing the pressing of the second shaft member $3b$, there is no need to pass the syringe dispenser 1 from one hand to the other for the second dispensing. Thus, the user is able to divide the amount of the content medium C into smaller fractions by one-hand operation. Especially in the present embodiment, the plunger 3 is configured by the first shaft member $3a$, which includes the piston 4 in the front end, and the second shaft member $3b$, which includes the bottomed tubular-shaped pressing shaft $3b_4$ configured to be fitted in the tubular portion $3a_9$ of the first shaft member $3a$. Furthermore, the engagement projection $3b_2$, which is provided on the outer circumferential surface of the second shaft member $3b$, is configured to engage with the opening $3a_8$ of the tubular portion $3a_9$. The above configurations allow the second shaft member $3b$ to be displaced smoothly in the axis O direction within the tubular portion's insertion hole $3a_{10}$ in response to pressing and to the pressing being released. Furthermore, with the engagement projection $3b_2$ being engaged, the second shaft member $3b$ is prevented from slipping out of the first shaft member $3a$. That is to say, the second shaft member $3b$ does not stagger or tilt with respect to the first shaft member $3a$ when the second shaft member $3b$ is pressed. Accordingly, operability of the syringe dispenser 1 at the time of pressing is improved.

Moreover, according to the present embodiment, the position of the front end surface $3f_3$ when the pressing of the second shaft member $3b$ is released is determined by the engagement projection $3b_2$ abutting against the opening $3a_8$ of the tubular portion $3a_9$. For the above reason, when the pressing of the second shaft member $3b$ is released, the resulting push-back does not excessively separate the front end surface $3f_3$ of the second shaft member $3b$ from the pressed surface $3a_7$. Accordingly, the second dispensing of the content medium C is achieved smoothly.

Moreover, according to the present embodiment, the slide projection $3a_2$ and the lock projection $3a_3$ are coupled by the thinned portion $3a_6$, which has a thickness in the radial direction that is reduced. Moreover, since in the present embodiment the pressing shaft $3b_4$ of the second shaft member $3b$ has the bottomed tubular shape with the front end surface $3f_3$ formed as the flat surface, the free end of each elastic piece $3a_1$, when being displaced in the inner circumferential direction, does not contact the second shaft member $3b$ from the radial direction. Thus, the lock projection $3a_3$ is configured to be displaced to a great extent toward the inner circumferential direction due to the restoring force when the pressing is released. The above configuration allows the large overlap allowance r between the lock projection $3a_3$ and the rear end of the flange portion $2d$ that helps stop the first dispensing of the content medium C (refer to FIG. 6B). Accordingly, the first dispensing of the content medium C may be stopped reliably.

Moreover, according to the present embodiment, with the tapered portion $3f_0$ disposed from a base portion to the slide projection $3a_2$, the elastic piece $3a_1$ is formed to have a thickness in the radial direction that is gradually increased. Due to the above configuration, the first shaft member $3a$ may be pushed in smoothly until the slide projection $3a_2$ slides on the inner circumferential surface $2f$ of the syringe 2 after the second shaft member $3b$ starts to be pressed.

Moreover, according to the present embodiment, the tapered surface $3f_2$ is disposed on the inner circumferential side of the pressing end surface $3f_1$. The above configuration allows the lock projection $3a_3$ to be displaced toward the inner circumferential direction along the tapered surface $3f_2$ easily when the pressing with the pressing end surface $3f_1$ is released.

Moreover, according to the present embodiment, the ribs $3a_{12}$, each of which is configured to engage with the inner circumferential end of the flange portion $2d$ in the corresponding position in which the pressing is started, are disposed on the outer circumferential surface of the first shaft member $3a$. The above configuration allows the user to grasp the positions of the plunger 3 in which the dispensing of the content medium C is started based on resistance against the pressing. Accordingly, the user will not dispense the content medium C by pushing in the plunger 3 erroneously in an unintended position.

Moreover, according to the present embodiment, since the tubular-shaped second shaft member $3b$ is configured to be inserted into the tubular portion's insertion hole $3a_{10}$ of the first shaft member $3a$, the plunger 3 is easy to assemble. Besides, the large-diameter groove $3a_{13}$ is provided in the tubular portion's insertion hole $3a_{10}$, and the large-diameter portion $3b_3$ is configured to be engaged in the large-diameter groove $3a_{13}$ of the first shaft member $3a$ when the second shaft member $3b$ is inserted into the tubular portion's insertion hole $3a_{10}$. The above configuration further improves the ease of assembly by allowing alignment in the circumferential direction to be performed at the same time as inserting the second shaft member $3b$ into the first shaft member $3a$.

Although various modes of the embodiment of the present disclosure have been described above, a variety of modifications are possible according to the present disclosure. For example, although the elastic piece $3a_1$ may be disposed in at least a single position, the elastic piece $3a_1$ is preferably disposed in plurality as in the present embodiment to reliably stop the plunger 3 and to accurately divide the amount of the content medium C into smaller fractions. Especially, arranging the pair of elastic pieces $3a_1$ in opposing positions as in the present embodiment allows favorable operation since stable balance is achieved around the axis line O. Although in the above embodiment the content medium C is described to be dispensed as a normal fluid, the content medium C may be dispensed in various manners such as in the form of foam or spray according to the present disclosure.

INDUSTRIAL APPLICABILITY

The present disclosure may be adopted in the syringe dispenser 1 with any of a variety of configurations which include the syringe 2 and the plunger 3 configured to be pushed into the syringe 2. The content medium C is not limited to the nasal drop, and a variety of content media C may be adopted.

REFERENCE SIGNS LIST

1 Syringe dispenser
2 Syringe
$2a$ Trunk
$2b$ Shoulder
$2c$ Front end portion
$2d$ Flange portion
$2d_0$ Syringe's rear end portion
$2f$ Inner circumferential surface
3 Plunger
$3a$ First shaft member
$3a_1$ Elastic piece
$3a_2$ Slide projection
$3a_3$ Lock projection
$3a_4$ Base portion
$3a_6$ Thinned portion
$3a_7$ Pressed surface
$3a_{70}$ Pressed flat surface
$3a_{71}$ Pressed tapered surface
$3a_8$ Opening
$3a_9$ Tubular portion
$3a_{10}$ Tubular portion's insertion hole
$3a_{11}$ Piston fixing male screw
$3a_{12}$ Rib
$3a_{13}$ Large-diameter groove
$3b$ Second shaft member
$3b_1$ Pressing flange
$3b_2$ Engagement projection
$3b_3$ Large-diameter portion
$3b_4$ Pressing shaft
$3f_0$ Tapered portion
$3f_1$ Pressing end surface (end surface)
$3f_2$ Tapered surface
$3f_3$ Front end surface
4 Piston
$A_1$ Front end through hole
$A_2$ Rear end opening portion
C Content medium
O Axis line
R Space
r Overlap allowance

The invention claimed is:

1. A syringe dispenser comprising: a syringe; and a plunger configured to be pushed into the syringe, wherein
the plunger includes a first shaft member including a piston at a front end thereof; and a second shaft member configured to be fitted in a tubular portion of the first shaft member,
the first shaft member includes at least one elastic piece extending toward a rear side, the elastic piece being provided with a slide projection and a lock projection, the slide projection being configured to enter through a rear end opening portion of the syringe and slide on an inner circumferential surface of the syringe, and the lock projection being configured to be locked against a rear end of the syringe,
the second shaft member includes a pressing shaft configured to be fitted in the tubular portion, the pressing shaft being provided in a front end thereof with an end surface configured to press a free end of the elastic piece, and the pressing shaft being also provided on an outer circumferential surface thereof with an engagement projection configured to engage with an engagement portion of the tubular portion to prevent the second shaft member from slipping out,
in response to pressing from the end surface, the free end of the elastic piece is restrained between the second shaft member and the syringe, and the elastic piece undergoes a flexure deformation starting from the slide projection, and thus, the lock projection is locked against the rear end of the syringe,
in response to the pressing being released, the locking of the lock projection is released due to a restoring force from the flexure deformation that starts from the slide projection, and
the slide projection and the lock projection are coupled by a thinned portion having a thickness in a radial direction that is reduced.

2. The syringe dispenser of claim 1, wherein the tubular portion is provided with an opening penetrating in a radial direction, and the elastic piece is arranged within the opening, with a rear end edge of the opening serving as the engagement portion.

3. The syringe dispenser of claim 1, wherein a position of the end surface when the pressing is released is determined by the engagement projection abutting against the engagement portion of the tubular portion.

4. The syringe dispenser of claim 2, wherein a position of the end surface when the pressing is released is determined by the engagement projection abutting against the engagement portion of the tubular portion.

5. The syringe dispenser of any one of claims 1 to 4, wherein the elastic piece, in a portion from a base portion to the slide projection thereof, is formed to have a thickness in a radial direction that is gradually increased.

6. The syringe dispenser of any one of claims 1 to 4, wherein the end surface is provided with a tapered surface.

7. The syringe dispenser of any one of claims 1 to 4, wherein the first shaft member is provided on an outer circumferential surface thereof with a rib configured to engage with the rear end of the syringe in a position in which the pressing is started.

* * * * *